US009528911B2

(12) United States Patent
Uratani et al.

(10) Patent No.: US 9,528,911 B2
(45) Date of Patent: Dec. 27, 2016

(54) ANALYSIS SYSTEM, INFORMATION PROCESSING DEVICE AND PROGRAM

(71) Applicant: HORIBA, Ltd., Kyoto (JP)

(72) Inventors: Katsumi Uratani, Kyoto (JP); Tsutomu Misogi, Kyoto (JP)

(73) Assignee: Horiba, Ltd., Kyoto (JP)

( * ) Notice: Subject to any disclaimer, the term of this patent is extended or adjusted under 35 U.S.C. 154(b) by 515 days.

(21) Appl. No.: 14/074,855

(22) Filed: Nov. 8, 2013

(65) Prior Publication Data

US 2014/0129157 A1    May 8, 2014

(30) Foreign Application Priority Data

Nov. 8, 2012    (JP) .................................. 2012-246267

(51) Int. Cl.
*G01M 15/10*    (2006.01)
*G01M 15/04*    (2006.01)
(Continued)

(52) U.S. Cl.
CPC ......... *G01M 15/102* (2013.01); *G01M 15/042* (2013.01); *G01N 1/2252* (2013.01); *G01N 35/00871* (2013.01)

(58) Field of Classification Search
CPC .............. G01M 15/102; G01M 15/142; G01N 35/00871; G01N 1/2252

(Continued)

(56) References Cited

U.S. PATENT DOCUMENTS 3,895,915 A * 7/1975 Haldeman .............. G01N 30/00
422/88
4,373,186 A * 2/1983 Marshall ............... G01M 15/05
701/102

(Continued)

FOREIGN PATENT DOCUMENTS

JP    04-033018    2/1992
JP    09133610    5/1997

(Continued)

OTHER PUBLICATIONS

Office Action dated May 28, 2015 issued for Japanese patent application No. 2012-246267, pp. 1-4.

(Continued)

*Primary Examiner* — Carol S Tsai
(74) *Attorney, Agent, or Firm* — Brooks Kushman P.C.

(57) ABSTRACT

The present invention is directed to an analysis system intended to be able to perform a unit setting of values over multi-pieces of analysis-associated data easily and systematically every analysis device, and the analysis system is provided with an analysis device and an information processing device, wherein the information processing device includes: a unit series data storage part adapted to store multi-pieces of unit series data composed by specifying units to be respectively used for values of the multi-pieces of analysis-associated data given and received between the analysis device and the information processing device; a selection input receiving part adapted to receive a selection input of any of the multi-pieces of the unit series data stored in the unit series data storage part; and a data output part adapted to output each of the values of the analysis-associated data in the unit specified to the selected unit series data.

8 Claims, 7 Drawing Sheets

(51) Int. Cl.
*G01N 1/22* (2006.01)
*G01N 35/00* (2006.01)

(58) Field of Classification Search
USPC ..... 702/50; 73/23.33, 23.31, 114.23, 114.71;
701/100, 102, 108, 114
See application file for complete search history.

(56) References Cited

U.S. PATENT DOCUMENTS

| | | | | |
|---|---|---|---|---|
| 5,708,585 | A * | 1/1998 | Kushion | G01F 1/692 422/51 |
| 7,107,142 | B2 * | 9/2006 | Harada | F02D 41/1406 701/114 |
| 7,328,606 | B2 * | 2/2008 | Nakamura | G01M 15/102 73/114.71 |
| 7,434,449 | B2 * | 10/2008 | Kusaka | G01N 1/2252 73/23.31 |
| 7,454,950 | B2 * | 11/2008 | Nakamura | G01N 33/0032 73/23.31 |
| 7,913,546 | B2 * | 3/2011 | Vinci | G01M 15/05 73/114.23 |
| 2002/0004694 | A1 * | 1/2002 | McLeod | G01M 15/05 701/31.4 |
| 2004/0117105 | A1 * | 6/2004 | Harada | F02D 41/1406 701/114 |
| 2006/0041368 | A1 * | 2/2006 | Williams | F02C 9/42 701/100 |
| 2006/0144124 | A1 * | 7/2006 | Kusaka | G01N 1/2252 73/23.33 |
| 2010/0126259 | A1 * | 5/2010 | Vinci | G01M 15/05 73/114.23 |
| 2011/0167047 | A1 * | 7/2011 | Arata | G06F 17/24 707/684 |

FOREIGN PATENT DOCUMENTS

| | | |
|---|---|---|
| JP | 09-170967 | 6/1997 |
| JP | 11-160204 | 6/1999 |
| JP | 2000-046705 | 2/2000 |
| JP | 2000-292315 | 10/2000 |
| JP | 2001-075693 | 3/2001 |
| JP | 2002-071528 | 3/2002 |

OTHER PUBLICATIONS

Kaoru Okada, Motor Exhaust Gas Analyzer MEXA-7000 Series 3.Data Processing System and Communications Line, Readout, No. 11, Sep. 1995, Japan, pp. 31-34.
Kiyoharu Abe, Manual on Unit Conversion Program Library UCL2, JAERI-M Report, Jul. 1981, JAERI-M 9592, pp. 1-92.
Mexa-One, (http://www.horiba.com/jp/corporate-news/news/article/mexa-one-8-19459/), May 24, 2012, 4 pgs.

* cited by examiner

AVAILABLE UNIT STORAGE PART

| PHYSICAL PHENOMENON TYPE NAME | UNIT NAME | UNIT NAME | ... | UNIT NAME |

...

| PHYSICAL PHENOMENON TYPE NAME | UNIT NAME | UNIT NAME | ... | UNIT NAME |

FIG.7

ANALYSIS SYSTEM, INFORMATION PROCESSING DEVICE AND PROGRAM

CROSS-REFERENCE TO RELATED APPLICATION

This application claims priority to JP Application No. 2012-246267, filed Nov. 8, 2012, the disclosure of which is incorporated in its entirety by reference herein.

TECHNICAL FIELD

The present invention relates to an analysis system for analyzing intake gas or exhaust gas of an internal combustion engine and to an information processing device and program to be used therefor.

BACKGROUND ART

An analysis system for an internal combustion engine of this type is composed of one or more analysis devices and an information processing device for managing these analysis devices. And multi-pieces of analysis-associated data such as measurement data and setting data are given and received between each of the analysis devices and the information processing device.

Unit systems for use in these multi-pieces of analysis-associated data are different according to users. For example, there may be some cases of using unit systems compliant with standards defined in countries or regions, or there may be also a case of using an originally own unit system.

Therefore, conventionally, there has been performed, for example, a work such that a unit system of analysis-associated data for use in an analysis system is previously set to be one used in a shipping destination user. Also, for example, in the case where certification tests in various countries are performed using this analysis system, there may be a case that the unit system of the analysis-associated data is changed by a user side every certification test in different countries.

However, even the analysis-associated data pertaining to one analysis device may be up to multi-pieces, and there may be a case where various types of analysis devices are used in one laboratory. In such a case, there is a problem that it takes much time and effort to set the unit system.

SUMMARY OF INVENTION

Technical Problem

Therefore, the present invention has been made in consideration of such a problem and its essential object is intended to be able to perform a unit setting of values over miscellaneous and multi-pieces of analysis-associated data easily and systematically every analysis device.

Solution to Problem

That is, an analysis system pertaining to the present invention is provided with at least one analysis device adapted to analyze intake gas or exhaust gas of an internal combustion engine and an information processing device that is communicatively connected to the analysis device.

Herein, the information processing device includes: a unit series data storage part adapted to store multi-pieces of unit series data composed by specifying units to be respectively used for values of multi-pieces of analysis-associated data given and received between the analysis device and the information processing device; a selection input receiving part adapted to receive a selection input of any of the multi-pieces of the unit series data stored in the unit series data storage part; and a data output part adapted to output each of the values of the analysis-associated data in the unit specified to the selected unit series data.

With this configuration, since each unit of the values of a series of analysis-associated data used in a certain analysis device can be collectively set and changed by simply selecting any of the unit series data associated with the analysis device, it is possible to greatly reduce the effort of the unit setting.

Moreover, since the collective unit setting and change can be performed every analysis device, it is easy to use the analysis system and a setting error can be prevented as much as possible.

As an embodiment aspect of rendering the effect of the present invention to be more remarkable, it can be exemplified that a plurality of the analysis devices are provided and the unit series data storage part stores multi-pieces of the unit series data while being classified with tie association in each of the analysis devices.

In order to increase the degree of freedom in setting, it is preferable that the information processing device is further provided with a unit series data editing part for editing contents of the unit series data storage part.

As a specific embodiment, it can be exemplified that the unit series data includes: an analysis-associated data name for identifying each of the analysis-associated data; a physical phenomenon type name indicating a physical phenomenon type such as a weight, length, volume and temperature associated with the analysis-associated data name; a unit name indicating the unit; and a number of output digits.

In order to facilitate the editing of the unit series data, it is preferable that the information processing device further includes an available unit storage part storing one or more unit names each of which is available for each of the physical phenomenon type names, and upon edition of the unit series data by the unit series data editing part, a unit name available for the physical phenomenon type set in the analysis-associated data is selected from among the unit names stored in the available unit storage part.

In order to increase the degree of freedom in setting the unit, it is preferable that the information processing device further includes a unit editing part for editing the available unit storage part.

In order to allow management of systematic analysis devices, it is preferable that the information processing device further includes an analysis device management part recognizing a plurality of analysis devices as one analysis device together in management.

Advantageous Effects of Invention

According to the present invention configured as described above, since each unit of the values of a series of analysis-associated data used in a certain analysis device can be collectively set and changed by simply selecting any of the unit series data associated with the analysis device, it is possible to greatly reduce the effort of the unit setting.

DESCRIPTION OF EMBODIMENTS

The following describes one embodiment of the present invention referring to the accompanying drawings.

Figure 1:
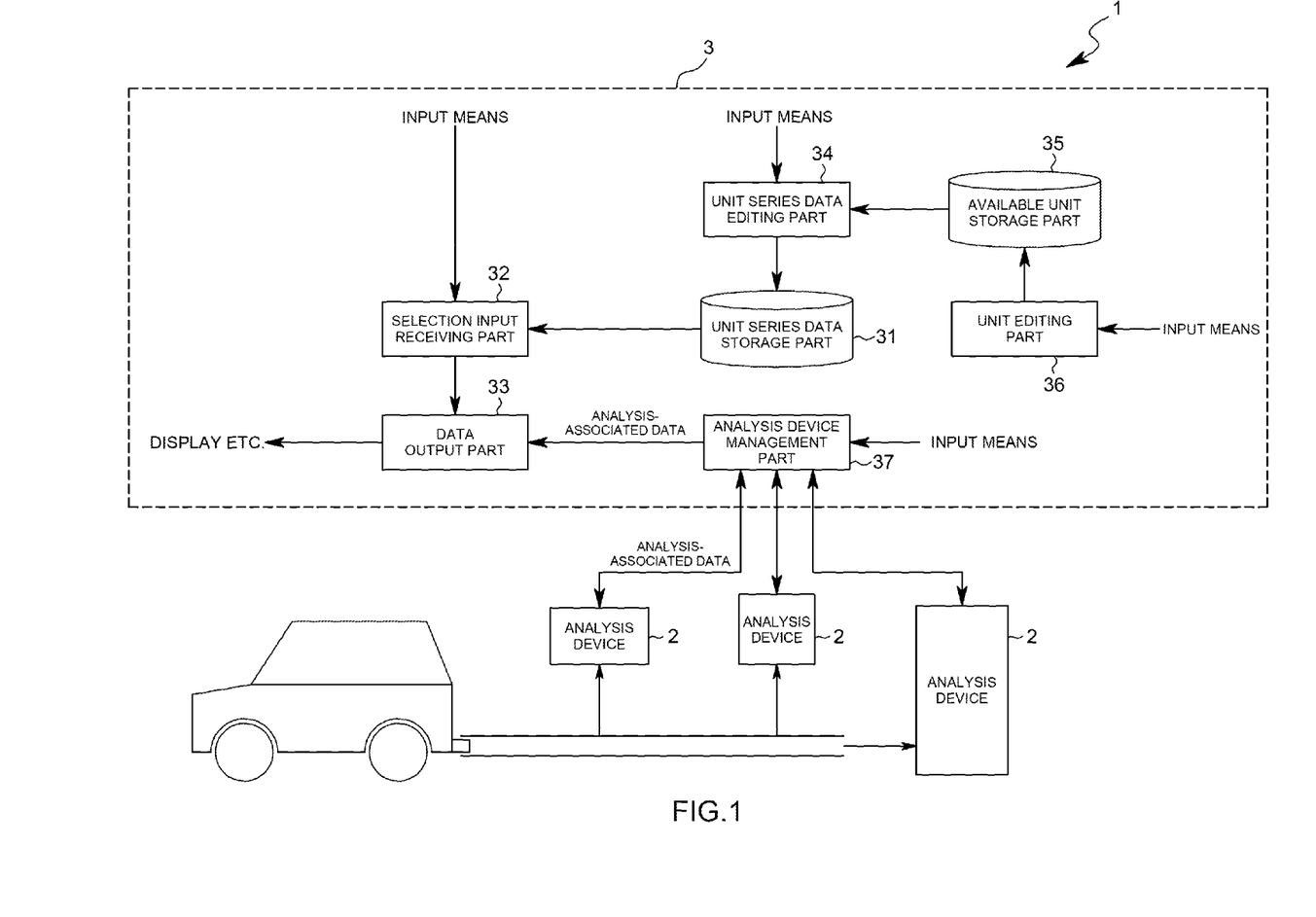
FIG. 1 is an overall configuration diagram of an analysis system in one embodiment of the present invention.

As shown in FIG. 1, an analysis system 1 pertaining to the present embodiment is intended to calculate an analysis component concentration, fuel consumption and the like by sampling exhaust gas of a vehicle internal combustion engine. This analysis system 1 includes a plurality of exhaust gas analysis devices 2 and an information processing device 3 for receiving measurement data measured by these analysis devices 2 or sending setting data to the analysis devices 2 to thereby integrally manage the analysis devices 2. It is noted that the measurement data and setting data etc. given and received between each of the analysis devices 2 and the information processing device 3 are referred to as "analysis-associated data" hereinafter.

The analysis devices 2 include, for example, a CVS device, EGR measurement device, exhaust gas comprehensive analysis device including a plurality of exhaust gas analysis units therein or the like and each of the analysis devices 2 outputs multi-pieces of measurement data. It is noted that, for convenience of management by the information processing device 3, the plurality of analysis devices may be recognized as one analysis device or may be vice versa. Also, the analysis devices may be configured as a hierarchically-structured management system. In the case of a hierarchically-structured configuration, various settings and the like as to be described later for the analysis devices in upper layers can be commonly effected to the analysis devices in lower layers. Meanwhile, the settings and the like as to be described later can be effected only for some of the analysis devices belonging to the lower layers.

The information processing device 3 is configured of, for example, a CPU (not shown), memory, A/D converter, D/A converter, communication interface, input means (such as a mouse and keyboard), display and the like. The CPU and peripheral equipment thereof are cooperated in accordance with a predetermined program stored in the memory, thereby performing functions as a unit series data storage part 31, selection input receiving part 32, data output part 33, unit series data editing part 34, available unit storage part 35, unit editing part 36, analysis device management part 37 and the like.

Next, the following describes a configuration of the analysis system 1 mentioned above, also serving as a detailed description of each of the parts.

The analysis-associated data described above is received by the data output part 33 via the analysis device management part 37 and is, for example, outputted to be displayed on the display or outputted to be filed. In this embodiment, an operator can set a unit of values of the outputted analysis-associated data using the input means.

Next, the setting of a unit is described in detail.

Figure 5:
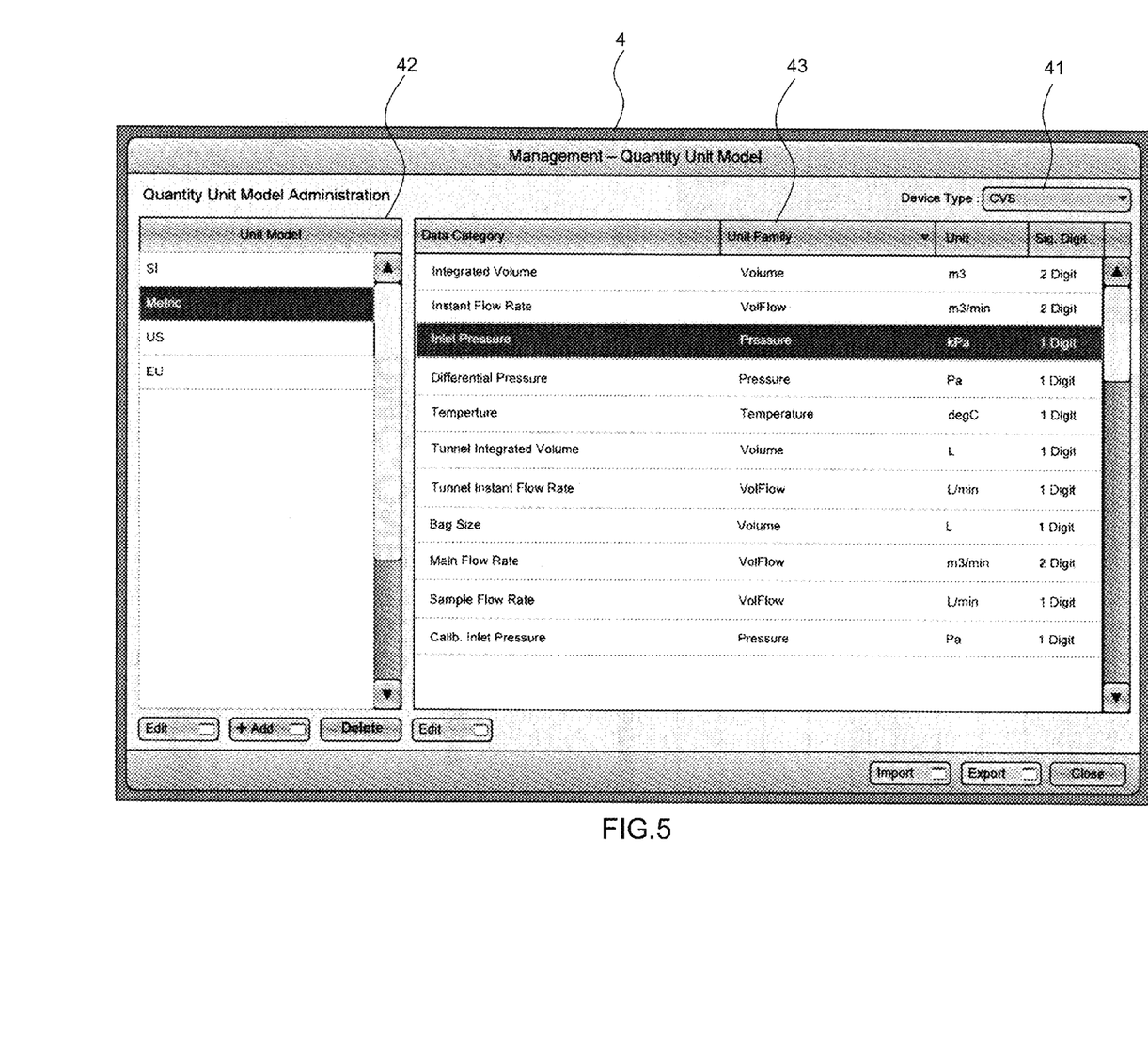
FIG. 5 is a screen configuration diagram showing one example of an editing screen in the same embodiment.

First, the selection input receiving part 32 displays a unit setting window 4 shown in FIG. 5 on the display referring to the unit series data storage part 31.

Figure 2:
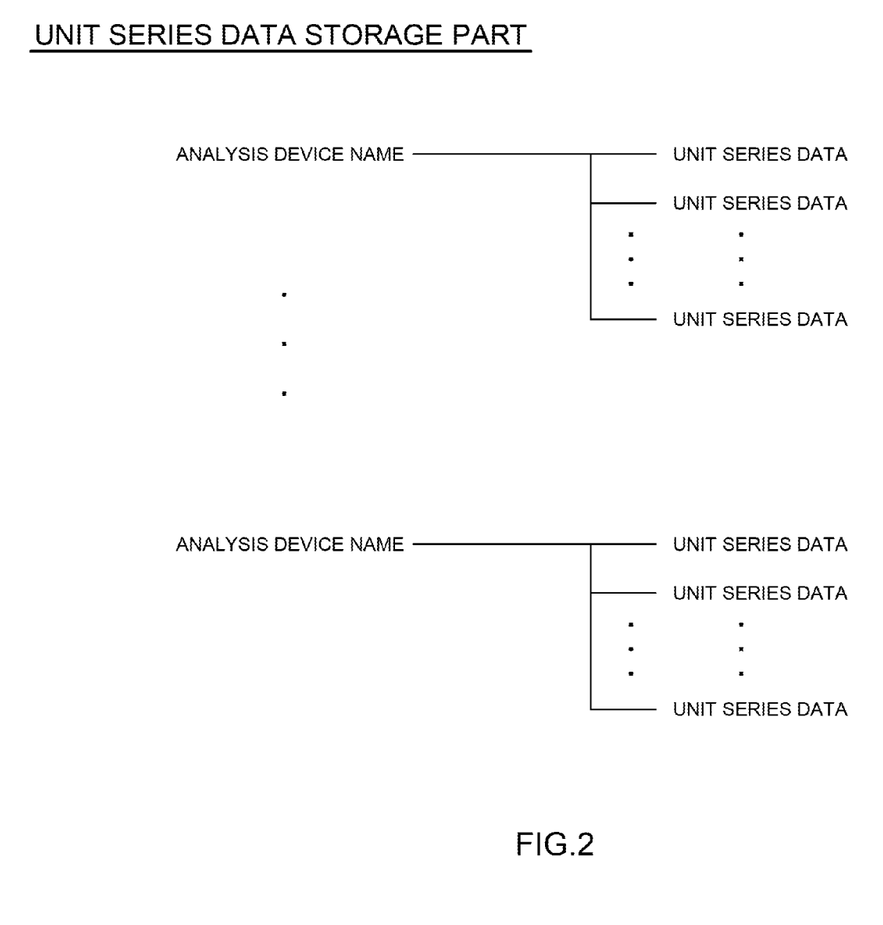
FIG. 2 is a data constitution diagram showing contents of a unit series data storage part in the same embodiment.
Figure 3:
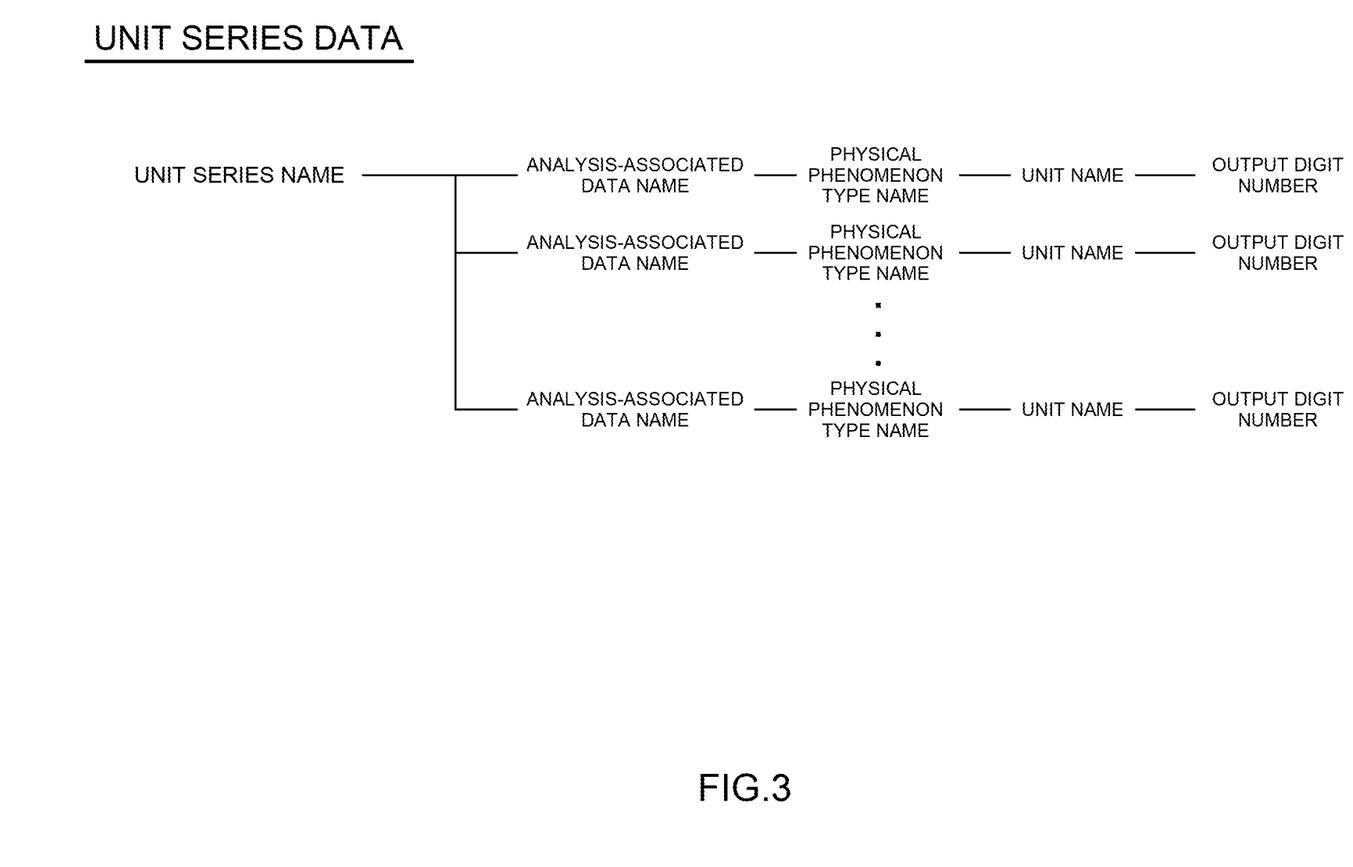
FIG. 3 is a data constitution diagram showing contents of unit series data in the same embodiment.
Figure 4:
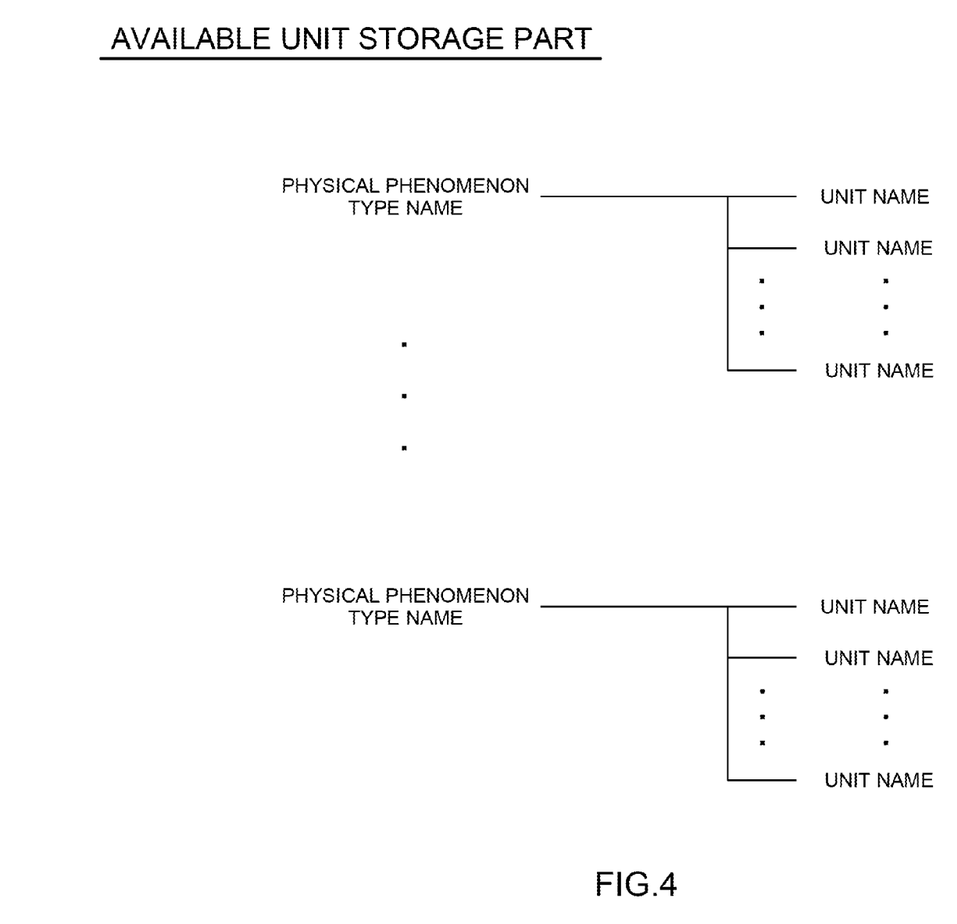
FIG. 4 is a data constitution diagram showing contents of an available unit storage part in the same embodiment.

More specifically, as shown in FIG. 2, multi-pieces of unit series data are stored in the unit series data storage part 31 with tie association in each of the analysis devices 2. As shown in FIG. 3, each unit series data includes a unit series name for identifying the unit series data and, in addition thereto, one or more analysis-associated data names (denoted as Data Category in FIG. 5) for identifying the analysis-associated data as substantive contents. In association with each of the analysis-associated data name, the unit series data further includes: a physical phenomenon type name (denoted as Unit Family in FIG. 5) indicating a physical phenomenon type such as a weight, length, volume and temperature; a unit name (denoted as Unit in FIG. 5) indicating the unit of the values of the outputted analysis-associated data; and a number of output digits (denoted as Sig. Digit in FIG. 5).

Thus, the unit setting window 4 is provided with: an analysis device name display column 41 for switchably displaying the analysis device name; a unit series name display column 42 for selectably displaying the unit series names in a list which can be used in the selected analysis device 2; a unit series data contents display column 43 for displaying the contents of the selected unit series data in a list, and the like. The selection input receiving part 32 displays: the analysis device names stored in the unit series data storage part 31 described above in the analysis device name display column 41; the unit series names in the unit series name display column 42; and the analysis-associated data names, physical phenomenon type names, unit names, and the output digit numbers in the unit series data contents display column 43.

In the unit setting window 4 displaying the above items in this way, regarding the analysis device 2 displayed in the analysis device name display column 41, it is indicated that the unit series data denoted to be active in the unit series name display column 42 is under selection. In the example shown in FIG. 5, the unit series data of the unit series name called Metric is selected for the analysis device named as CVS.

In this state, when an operator selects another unit series name displayed in the unit series name display column 42 using, for example, a mouse, the contents of the unit series data is displayed in a list in the unit series data contents display column 43. Then, although not shown, when a deciding operation is performed by the operator, the selection input receiving part 32 receives the selected unit series data.

Then, the data output part 33 displays the values of the analysis-associated data in each unit specified for the selected unit series data, for example, on the display, respectively (not shown).

Figure 6:
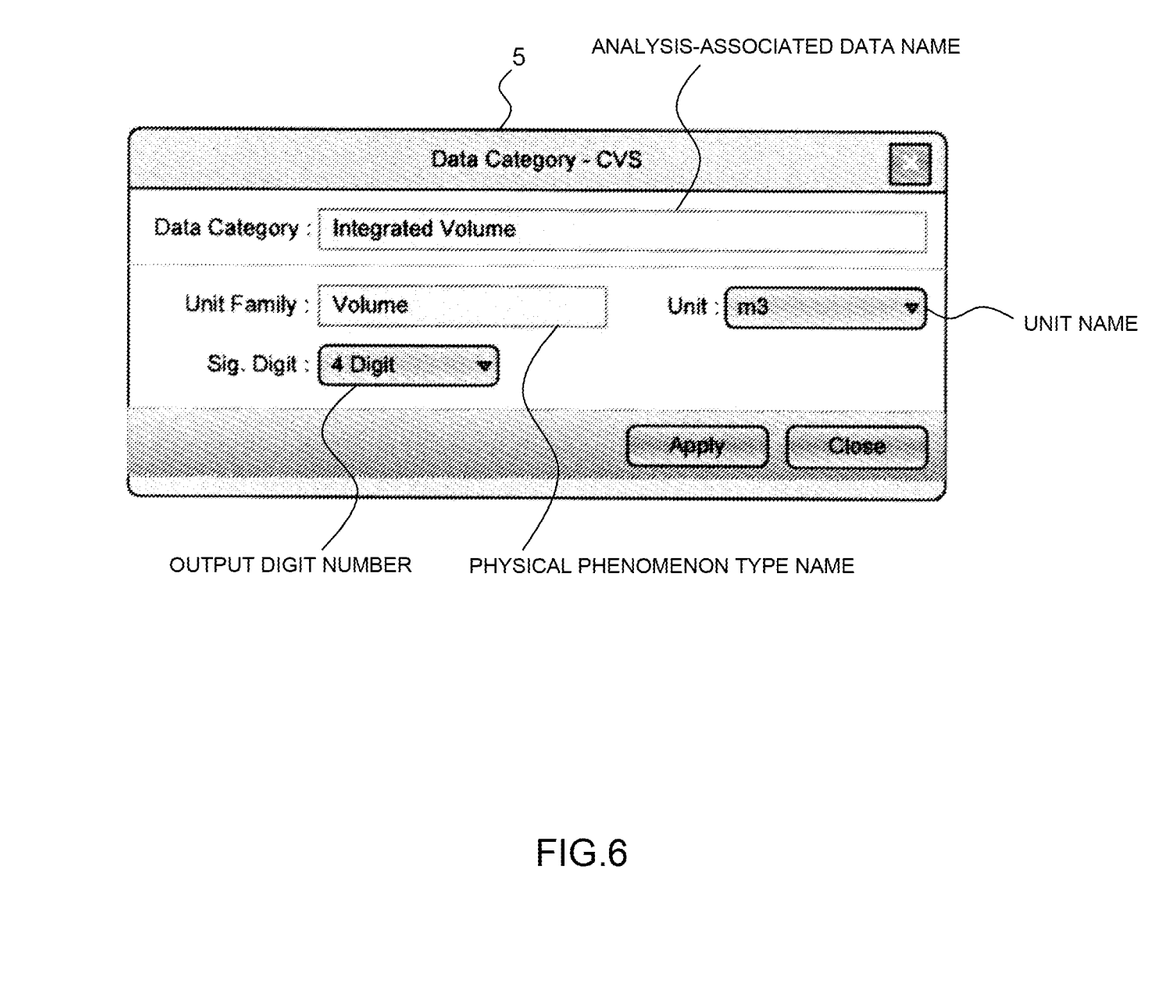
FIG. 6 is a screen configuration diagram showing one example of an editing screen in the same embodiment.

Further, in the present embodiment, the contents of the unit series data storage part 31 can be edited. For that purpose, the operator performs an appropriate operation such as clicking an EDIT button of the unit setting window 4. Then, a unit series data editing window 5 shown in FIG. 6 is displayed so as to be able to change the contents of each unit series data associated with each of the analysis devices 2, i.e., the analysis-associated data name, physical phenomenon type name, unit name and number of output digits. Then, the unit series data editing part 34 reads the contents selected by the operator in this operation and changes the contents of the unit series data storage part 31. Further, in FIG. 6, it is configured to be able to select the unit name and the number of output digits from among a previously registered list.

In addition, the unit series data can be increased by clicking an ADD button shown in FIG. 5, and the unit series data can be also deleted by clicking a DELETE button shown in FIG. 5.

Figure 7:
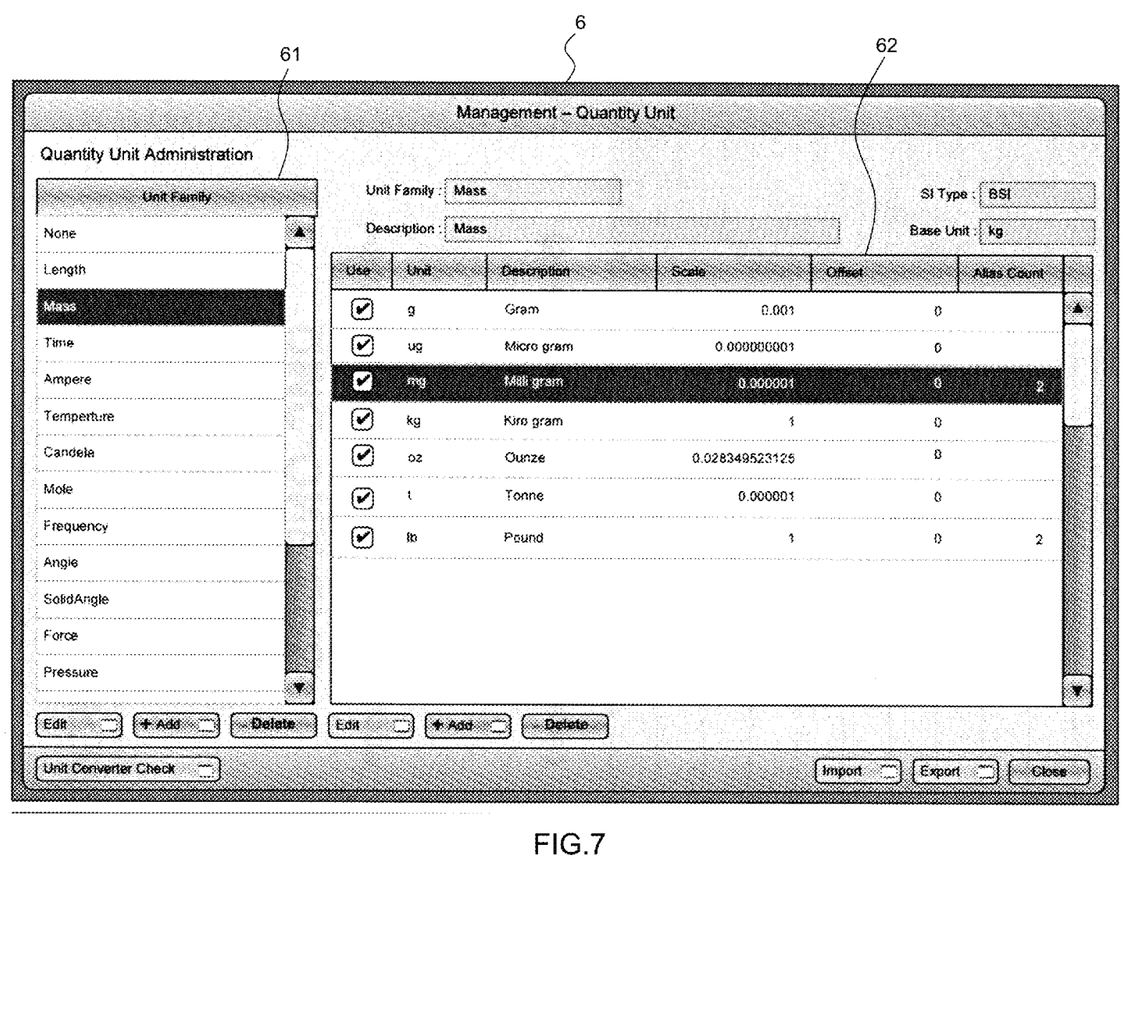
FIG. 7 is a screen configuration diagram showing one example of an editing screen in the same embodiment.

In addition, the contents of this available unit storage 35 can be also edited by an operator. In that case, an available unit editing window 6 shown in FIG. 7 is displayed by an appropriate operation by the operator. A physical phenomenon type name list column 61 is provided in this available unit editing window 6, and upon selection of one physical phenomenon type name in the list column 61, one or more unit names available in the selected physical phenomenon type are displayed in a list in an available unit column 62. Among the listed unit names, those unit names having checked in check boxes are available, and upon taking off a check, the corresponding unit name can be made unavailable. A scale of the unit is also editable. The unit editing part 36 reads this operation and edits the available unit storage part 35.

With this configuration, since each unit of the values of a series of analysis-associated data used in a certain analysis device can be collectively set and changed by simply selecting any of the unit series data associated with the analysis device, it is possible to greatly reduce the effort of the unit setting.

Further, since it is possible to add, change or delete a unit any time in accordance with a need of an operator using the unit series data editing part 34 and unit editing part 36, a flexible operation becomes possible.

In addition, the present invention should not be limited to the above embodiment, and various modifications such as configurations of the respective windows are possible within the scope unless departing from the intended spirit thereof.

DESCRIPTION OF REFERENCE NUMERALS

1 . . . Analysis system
2 . . . Analysis device
3 . . . Information processing device
31 . . . Unit series data storage part
32 . . . Selection input receiving part
33 . . . Data output part
34 . . . Unit series data editing part
35 . . . Available unit storage part
36 . . . Unit editing part
37 . . . Analysis device management part

What is claimed is:

1. An analysis system provided with at least one analysis device adapted to analyze intake gas or exhaust gas of an internal combustion engine and an information processing device that is communicatively connected to the analysis device, wherein
the information processing device comprises:
a unit series data storage part adapted to store multi-pieces of unit series data composed by specifying units to be respectively used for values of multi-pieces of analysis-associated data given and received between the analysis device and the information processing device, wherein the unit series data includes an analysis-associated data name for identifying each of the analysis-associated data, a physical phenomenon type name indicating a physical phenomenon type such as a weight, volume and temperature associated with the analysis-associated data name, a unit name indicating the unit, and a number of output digits;
a selection input receiving part adapted to receive a selection input of any of the multi-pieces of the unit series data stored in the unit series data storage part; and
a data output part adapted to output each of the values of the analysis-associated data in the unit specified to the selected unit series data.

2. The analysis system according to claim 1, wherein a plurality of analysis devices are provided and the unit series data storage part stores multi-pieces of the unit series data with tie association in each of the analysis devices.

3. The analysis system according to claim 1, wherein the information processing device is further provided with a unit series data editing part for editing contents of the unit series data storage part.

4. The analysis system according to claim 3, wherein the information processing device further comprises an available unit storage part storing one or more unit names each of which is available for each of the physical phenomenon type names, and upon edition of the unit series data by the unit series data editing part, a unit name available for the physical phenomenon type set in the analysis-associated data is selected from among the unit names stored in the available unit storage part.

5. The analysis system according to claim 4, wherein the information processing device further comprises a unit editing part for editing the available unit storage part.

6. The analysis system according to claim 1, wherein the information processing device further comprises an analysis device management part recognizing a plurality of analysis devices as one analysis device together in management.

7. An information processing device for an analysis system communicatively connected to an analysis device adapted to analyze intake gas or exhaust gas of an internal combustion engine, the information processing device comprising:
a unit series data storage part adapted to store multi-pieces of unit series data composed by specifying units to be respectively used for values of multi-pieces of analysis-associated data given and received between the analysis device and the information processing device, wherein the unit series data includes an analysis-associated data name for identifying each of the analysis-associated data, a physical phenomenon type name indicating a physical phenomenon type such as a weight, length, volume and temperature associated with the analysis-associated data name, a unit name indicating the unit, and a number of output digits;
a selection input receiving part adapted to receive a selection input of any of the multi-pieces of the unit series data stored in the unit series data storage part; and
a data output part adapted to output each of the values of the analysis-associated data in the unit specified to the selected unit series data.

8. A program implemented in an information processing device for an analysis system communicatively connected to an analysis device adapted to analyze intake gas or exhaust gas of an internal combustion engine, the program allowing the information processing device to exerting functions of:
a unit series data storage part adapted to store multi-pieces of unit series data composed by specifying units to be respectively used for values of multi-pieces of analysis-associated data given and received between the analysis device and the information processing device, wherein the unit series data includes an analysis-associated data name for identifying each of the analysis-associated data, a physical phenomenon type name indicating a physical phenomenon type such as a weight, length, volume and temperature associated with the analysis-associated data name, a unit name indicating the unit, and a number of output digits;

a selection input receiving part adapted to receive a selection input of any of the multi-pieces of the unit series data stored in the unit series data storage part; and a data output part adapted to output each of the values of the analysis-associated data in the unit specified to the selected unit series data.

\* \* \* \* \*